United States Patent [19]
Mortellite et al.

[11] Patent Number: 5,942,080
[45] Date of Patent: Aug. 24, 1999

[54] APPARATUS FOR STRIP LAMINATION OF A POLYMER FILM AND NON-WOVEN WEBS

[75] Inventors: Robert M. Mortellite, Maineville; Kevin W. Preston, Loveland; Thomas G. Mushaben, Cincinnati, all of Ohio

[73] Assignee: Clopay Plastic Products Company, Inc., Cincinnati, Ohio

[21] Appl. No.: 08/722,286

[22] Filed: Oct. 9, 1996

Related U.S. Application Data

[63] Continuation-in-part of application No. 08/547,059, Oct. 23, 1995, abandoned.

[51] Int. Cl.$^6$ .................................................. B31F 7/00
[52] U.S. Cl. .................. 156/461; 156/470; 156/500; 156/502; 156/504; 156/505; 156/510; 156/516; 156/204; 242/555.3; 242/555.6
[58] Field of Search ............... 156/265, 244.18, 156/244.19, 271, 500, 510, 516, 253, 517, 204, 201, 200, 199, 227, 210, 207, 555, 205, 461, 470, 501, 504, 505, 502; 242/555.3, 555.6, 556, 556.1

[56] References Cited

U.S. PATENT DOCUMENTS

| | | | |
|---|---|---|---|
| 2,897,108 | 7/1959 | Harwood | 154/50 |
| 3,411,419 | 11/1968 | Becker et al. | 156/271 |
| 3,477,126 | 11/1969 | Price | 29/605 |
| 3,494,001 | 2/1970 | Banks | 19/145 |
| 3,503,106 | 3/1970 | Port et al. | 28/72 |
| 3,540,959 | 11/1970 | Connor | 156/203 |
| 3,656,513 | 4/1972 | Evans et al. | 138/141 |
| 3,785,897 | 1/1974 | Zipf, III | 156/201 |
| 3,919,377 | 11/1975 | Dow et al. | 264/40.1 |
| 4,129,632 | 12/1978 | Olson et al. | 264/40.1 |
| 4,256,791 | 3/1981 | Holmström et al. | 428/77 |
| 4,859,259 | 8/1989 | Scheibner | 156/66 |
| 4,915,282 | 4/1990 | Martin et al. | 226/119 |
| 5,253,819 | 10/1993 | Butler, Jr. | 242/58.3 |
| 5,422,172 | 6/1995 | Wu | 428/230 |
| 5,540,796 | 7/1996 | Fries | 156/164 |
| 5,567,260 | 10/1996 | McFall | 156/201 |
| 5,601,546 | 2/1997 | Tahji et al. | 604/385.2 |
| 5,656,111 | 8/1997 | Dilnik et al. | 156/66 |
| 5,714,027 | 2/1998 | Taub | 156/204 |
| 5,759,317 | 6/1998 | Justmann | 156/66 |
| 5,800,654 | 9/1998 | Davis et al. | 156/227 |

FOREIGN PATENT DOCUMENTS

| | | | |
|---|---|---|---|
| 0088738 | 9/1983 | European Pat. Off. | 156/227 |
| 0316875 | 5/1989 | European Pat. Off. | 156/256 |
| 2209520 | 5/1994 | France | 156/256 |
| 59-74848 | 4/1984 | Japan | 156/256 |
| 2154494 | 9/1985 | United Kingdom | 156/256 |
| 2193734 | 2/1988 | United Kingdom | 156/201 |
| 9500092 | 1/1995 | WIPO | 156/201 |

*Primary Examiner*—David A. Simmons
*Assistant Examiner*—Linda L Gray
*Attorney, Agent, or Firm*—Wood, Herron & Evans, L.L.P.

[57] ABSTRACT

An apparatus for lamination of a non-woven fibrous sheet and an extruded polymer sheet including a web slitter to divide the fibrous sheet into a plurality of webs, a plurality of folding means to fold each web, a plurality of separated turning bars to turn each folded web such that the webs are separated, and an extrusion laminator for laminating the polymer sheet to the separated webs to provide a laminate having a portion of the polymer sheet between the separated webs.

23 Claims, 7 Drawing Sheets

APPARATUS FOR STRIP LAMINATION OF A POLYMER FILM AND NON-WOVEN WEBS

This Application is a continuation in part of U.S. patent application Ser. No. 08/547,059, filed Oct. 23, 1995, now abandoned, entitled APPARATUS AND PROCESS FOR STRIP LAMINATION OF A POLYMER FILM AND NON-WOVEN OR WOVEN WEBB.

BACKGROUND OF THE INVENTION

Processes of laminating polymer films over spaced narrow webs are known. Relevant patents regarding lamination of narrow spaced webs include U.S. Pat. Nos. 3,477,126, 3,656,513 and 4,859,259. The '126 patent discloses a method of making a strip conductor material where webs of aluminum, which are spaced apart on a roll, are unrolled and an extruder applies a layer of plastic material to one side of the webs. The wide extruded layer is later slit to form individual aluminum webs with the plastic material covering one surface of the individual webs and overhanging both sides. The '513 patent discloses a method of manufacturing strip material for fabricating container bodies wherein a single wide roll of cardboard is slit, skived and extrusion coated with plastic on both sides. The '513 patent shows turning bars for steering the individual cardboard strips into subsequent manufacturing processes after the webs have been slit and laminated. The '259 patent discloses a process and apparatus for fabricating re-closable plastic bags wherein a double set of interlocking closure strips are unrolled from a reel, the strips are separated and a polymer film is extruded onto the strips. The polymer film is then slit, folded around a folding apparatus and wound upon reels.

Processes of dynamically bonding thermoplastic films are also known. U.S. Pat. No. 4,919,738 herein incorporated by reference teaches a method and apparatus for dynamically mechanically bonding laminate layers, including at least one thermoplastic layer, by a pressure biased nip and an opposed roller.

SUMMARY OF THE INVENTION

The present invention is directed to a method and apparatus for laminating polymer to another material where the polymer has a different width than the material to which it is laminated.

One aspect of the present invention is directed to process and apparatus for laminating a wide web of nonwoven with narrow strips of polymer.

Another aspect of the invention is directed to a process and apparatus to continuously perform web splitting, folding, guiding and laminating steps in a single unit. A single wide web of nonwoven is slit, folded, spaced apart by a predetermined distance by the use of turning bars and steered into a subsequent lamination process. Depending on the spacing between folded webs, each strip of polymer may include a loose flap on either side which may be suitable for forming a barrier cuff in a diaper or other hygiene product. The spacing between folded webs determines the width of a loose polymer flap which is formed.

Yet another aspect of the invention is directed to a process and apparatus to continuously perform web splitting, separating, guiding and laminating steps in a single unit. A single wide web is slit, separated by the use of turning bars and steered into a subsequent lamination process.

This invention provides an apparatus and method of producing the laminate on high speed production machines at line speeds of about 300–1,200 feet per minute (fpm). It involves in-line slitting of a single wide web of material, turning, separating, and subsequently laminating the webs. More specifically, a web is unrolled from a wide roll of nonwoven material. The incoming web is slit into narrow webs by score slitting, shear slitting, razor slitting, laser, water jet slitting or ultrasonic slitting, the narrow webs, which may be folded at a folding plate, then move down the line to turning bars which are displaced one from the other by a desired web separation distance. The spaced webs are then guided to an embossing or laminating station where the spaced webs are fed through nip rollers to adhere molten or solid polymer to the webs. More specifically, the webs may be introduced into a nip of rollers for extrusion lamination with a polymer film or may be dynamically mechanically bonded to a solid polymer film. When laminating the nonwoven to a polymer extrudate, the extrudate is extruded into the nip at a temperature above its softening point to form a film. The compressive force between the webs and the extrudate at the nip is controlled to bond one surface of the web to the film to form the laminate. The wide laminate layer is then slit and may be unfolded prior to winding on a take-up reel. When Laminating to a solid film of polymer the film may be slit and separated, as described above, and then dymanically bonded to a wide nonwoven web.

Other benefits, advantages and objectives of this invention will be further understood with reference to the following detailed description.

DETAILED DESCRIPTION OF THE DRAWINGS

Figure 1:
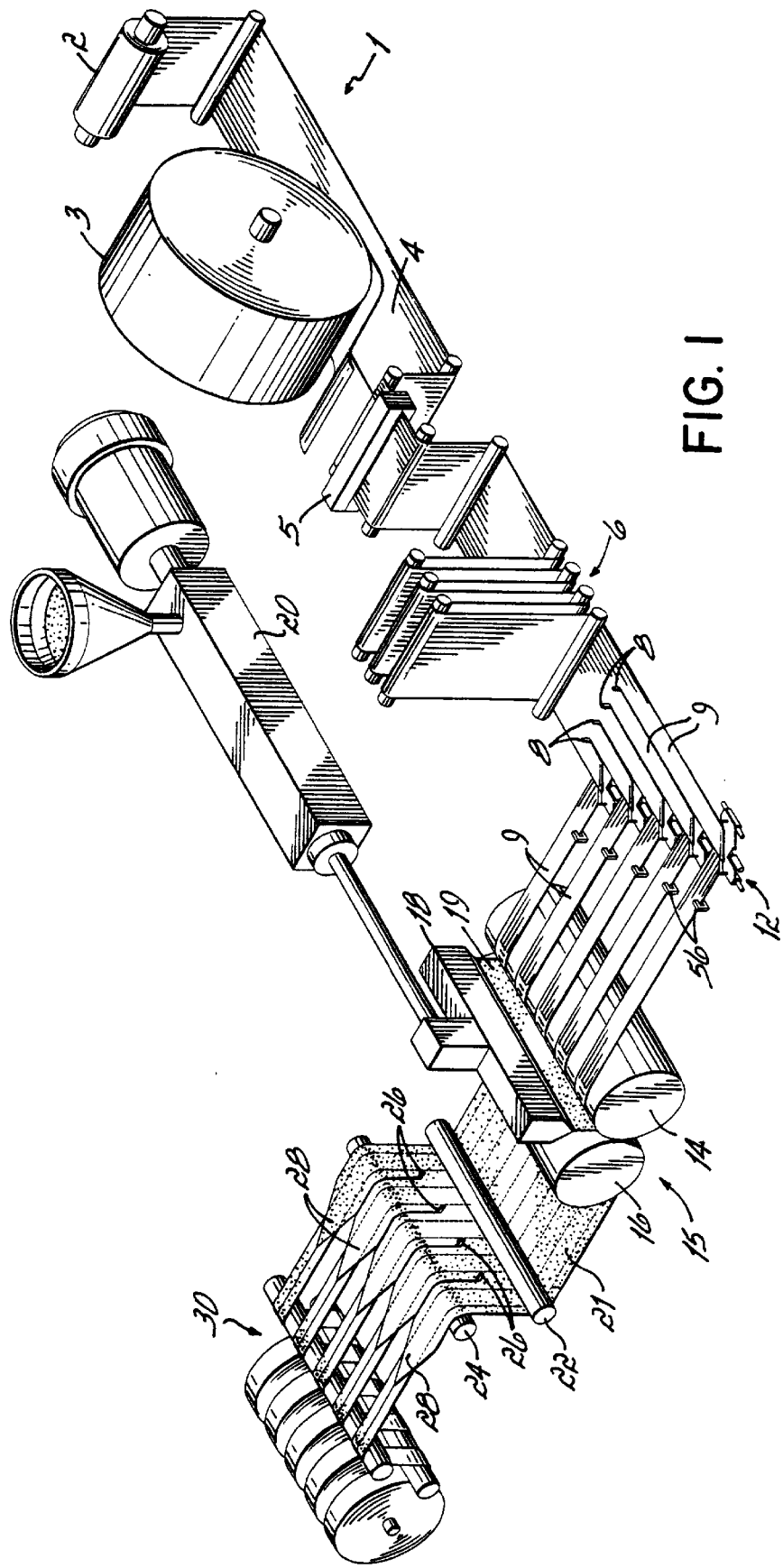
FIG. 1 is a diagrammatic perspective view of an in-line apparatus for slitting, turning and separating a nonwoven web with subsequent extrusion laminating.

It is a primary objective of this invention to provide a method and apparatus for forming a plurality of spaced laminated strips of nonwoven web material and polymer film on high speed production machinery. The laminate strips are characterized by being impervious to the passage of fluid by virtue of the polymer film while maintaining a soft feel on the fibrous web surface of the laminate. It is another objective of this invention to provide a method and apparatus for forming a wide strip of nonwoven with a narrow strip of polymeric material laminated thereto. Another objective of the present invention is to provide a product having a wide strip of nonwoven with a narrow strip of polymeric material laminated thereto.

In a first embodiment of the present invention a nonwoven web is used to provide an inexpensive waterproof laminate which has a soft hand. In another embodiment, an elastic fabric web is used to provide stretch qualities desired. In yet another embodiment, a polymer web may be laminated to the polymer film to provide a double polymer film laminate. Various degrees of vapor or air permeability may be achieved in the laminate, for instance, by providing mechanical microvoids.

In a preferred form, the laminate produced by the present invention has the desirable feature of soft feel to achieve utility in a number of applications including diapers, underpads, sanitary napkins or other products. In another form of the invention, the laminate of the present invention includes loose flaps of polymeric material which is suitable for use as a barrier cuff.

The polymer film is preferably a thermoplastic polymer that is processable into a film for direct lamination by melt extrusion onto the nonwoven web in one embodiment. Suitable polymers for the film include polyethylene, polypropylene, poly(ethylene-butene), poly(ethylene-hexene), poly(ethylene-octene), poly(ethylene-propylene), poly(styrene-butadiene-styrene), poly(styrene-isoprenestyrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene-butylacrylate), polyurethane, poly(ethylene-propylene-diene), ethylene-propylene rubber. A new class of rubber-like polymers may also be employed and they are generally referred to herein as polyolefins produced from single-cite catalysts. The most preferred catalysts are known in the art as metallocene catalysts whereby ethylene, propylene, styrene and other olefins may be polymerized with butene, hexene, octene, etc., to provide elastomers suitable for use in accordance with the principles of this invention, such as poly(ethylene-butene), poly(ethylene-hexene), poly(ethylene-octene), poly(ethylene-propylene) and/or polyolefin terpolymers thereof.

Suitable thermoplastic polymers may be biodegradable or environmentally degradable. A number of biodegradable thermoplastic polymers suitable in the practice of the invention are of the normally-solid oxyalkanoyl polymers or dialkanoyl polymers represented by poly(caprolactone) or poly(ethylene adipate); polysaccharides or modified polysaccharides such as starch-resin compositions that may be film-formed. Suitable thermoplastic polymers that may also be environmentally degradable include polyolefin based polymers that may be film-formed into water insoluble and impermeable films for use as barrier materials in the manufacture of many useful articles such as diapers, underpads, packaging, drapes and the like. The olefin based polymers include the most common ethylene or propylene based polymers such as polyethylene, polypropylene, and copolymers such as ethylene vinylacetate (EVA), ethylene methyl acrylate (EMA) and ethylene acrylic acid (EAA), or blends of such polyolefins. The olefins that may be polymerized alone or in admixture with other ethylenically unsaturated monomers include, e.g., ethylene; propylene; 1-butene; isobutene; 1-pentene; halogenated olefins such as chloroprene; vinyl benzenes and naphthalenes such as styrene or vinyl naphthalene; vinyl or vinylidene halides such as vinyl chloride and vinylidene chloride; vinyl esters such as vinyl acetate and vinyl benzoate; acrylic and methacrylic acids (otherwise known as polyacrylate of methacrylate) and esters or amides thereof; and dienes such as butadiene, isoprene and cyclopentadiene. Other examples of polymers suitable for use as films in the composite sheet of this invention are known and referenced in relevant patents regarding extrusion lamination of nonwoven webs including U.S. Pat. Nos. 2,714,571; 3,058,863; 4,522,203; 4,614,679; 4,692,368; 4,753,840 and 5,053,941 herein incorporated by reference.

The web may be a fibrous nonwoven web comprising fibers of polyethylene, polypropylene, polyesters, rayon, cellulose, nylon, and blends of such fibers. A number of definitions have been proposed for nonwoven fibrous webs. The fibers are usually staple fibers or continuous filaments. As used herein "nonwoven fibrous web" is used in its generic sense to define a generally planar structure that is relatively flat, flexible and porous, and is composed of staple fibers or continuous filaments. For a detailed description of nonwovens, see "Nonwoven Fabric Primer and Reference Sampler" by E. A. Vaughn, Association of the Nonwoven Fabrics Industry, 3d Edition (1992). The nonwovens may be carded, spun bonded, wet laid, air laid and melt blown as such products are well known in the trade.

Alternatively, the web may be a woven fabric having elastic qualities which may be imparted to the final laminated product. It is also possible to laminate a polymer web to the extruded polymer to form a multi-layer polymer laminate.

The following examples illustrate the process of making the laminates of the present invention and the processing machinery used in such methods. In light of these examples and this further detailed description, it is apparent to a person of ordinary skill in the art that variations thereof may be made without departing from the scope of this invention.

EXAMPLE 1

A carded polypropylene nonwoven fibrous web of 26 g/yd$^2$ density is loaded into the unwind position. The wide web is then fed through the zero speed thermal splicer and festoon and slit into a plurality of adjacent narrow webs. At a line speed of 500 FPM the narrow webs are then spaced apart by being turned about the spaced turning bars. The web guides then steer the narrow webs to the laminating station where the webs are laminated by extrusion of an LDPE thermoplastic film with a density of 0.914 g/cc at 1 mil. The LDPE film is extruded through a die at about 625° F. and into the nip rollers which press on the webs and LDPE film at about 30 psi. The LDPE thermoplastic film is then slit and folded back upon itself and wound around the winder for storage or later use.

EXAMPLE 2

In this Example the same procedures are followed as in Example 1, except the plastic used for extrusion is DOW Chemical elastomer incite resin XU51800.51 with a density of 0.870 grams per cubic centimeter.

EXAMPLE 3

A carded polypropylene having a density of 34 grams/yd$^2$ is loaded, slit and separated as in example 1, but at a line speed of about 1000 FPM, and coated with EVA copolymer at about 1.0 mil. The EVA film is extruded through a die at 500° F. and into the nip rollers which press on the webs and EVA film at 80 psi.

EXAMPLE 4

A carded polypropylene nonwoven having a density of 34 g/yd$^2$ is loaded, slit and separated as in example 1, but at a line speed of about 750 FPM, and coated with EVA copolymer at about 2.0 mils. The EVA film is extruded through a die at 570° F. and into the nip rollers which press on the webs and EVA film at 10 psi.

EXAMPLE 5

A carded polypropylene nonwoven having a density of 41 g/yd$^2$ is extrusion laminated with 2 mil of EPDM elastomer at a line speed of about 850 FPM. The EPDM film is extruded through a die at about 540° F. and into the nip rollers which press on the webs and EVA film at about 40 psi.

EXAMPLE 6

DU PONT SONTARA polyester fabric grade 8000 is extrusion laminated to 1 mil of DU PONT polyester elastomer (HYTREL 8260) at a line speed of about 950 FPM. The HYTREL film is extruded through a die at about 580° F. and into the nip rollers which press on the webs and HYTREL film at about 60 psi.

EXAMPLE 7

EXXON EXACT polymer type 4011 of ethylene and octene manufactured by using a Metallocene catalyst a density of 0.885 g/cc extrusion laminated to DU PONT's polyester SONTARA fabric grade 8000 at a line speed of about 700 FPM. The EXACT film is extruded through a die at about 530° F. and into the nip rollers which press on the webs and EVA film at about 50 psi.

EXAMPLE 8

A carded polypropylene nonwoven fibrous web of 20 grams/yd$^2$ is loaded into the unwind position. The wide web of this nonwoven roll is then fed through the slitting station to form multiple adjacent webs approximately 14 inches wide. Each 14 inch wide web is then folded approximately 3.5 inches from the free edges of slit nonwoven toward the center of the nonwoven, so that both edges abut one another. The folded nonwoven webs are steered to the desired spacing to each other, i.e., 0.25 inch wide by spaced turning bars which are controlled by web guides. The spaced and folded nonwoven webs are then fed to an extrusion laminating station and laminated by extrusion of a polyethylene film of 0.914 grams/cm$^3$. This polyethylene film having a thickness of approximately 0.8 mils is extruded through a conventional extrusion die, at a melt temperature between 400°–600° F., into the nip rollers which press on the webs and polyethylene film with approximately 30–60 psi of pressure to achieve the desired bond strength of between 10 grams/inch to several hundred grams/inch of peel strength.

The laminate then enters a slitting station where slitting knives are located between the folded nonwoven webs to slit the polyethylene film. Accordingly, the 7 inch folded nonwoven webs are all laminated to polyethylene film of 7.25 inches wide. The 7 inch nonwoven web is laminated with polyethylene film with a 0.125 inch wide loose flap of polyethylene film on each side of the nonwoven which is not laminated to nonwoven. The strip laminated, folded nonwoven is wound directly onto a roll for storage or later use.

EXAMPLE 9

The non-woven is slit and folded as in Example 8. However, the spacing between each folded web is adjusted to approximately 4" wide. The slitting knives are located between adjacent folded nonwoven webs to split the polymer into 11 inch widths. The result is a nonwoven web of 14" width which is covered with an 11 inch wide polymeric film where 7 inch width of this film is laminated to the 7 inches at the center of the folded nonwoven. The additional polyethylene film of 2" on opposite sides of the laminated nonwoven, which is not laminated to the nonwoven web, may be used to construct barrier cuffs to provide a self-contained pocket to confine body waste.

EXAMPLE 10

A carded polypropylene nonwoven fibrous web of 20 grams/yd$^2$ is loaded into the unwind position. The wide web of this nonwoven roll is then fed through a slitting station to form multiple adjacent webs approximately 14 inches wide. Each 14 inch wide web is then folded approximately 3.5 inches from the free edges of slit nonwoven toward the center of the nonwoven, so that both edges abut one another. This 7 inch wide web is the folded a second time approximately 1.75 inches from the outer edge so that the folded edges abut one another. The folded nonwoven webs are then steered to the desired spacing to each other, i.e., 0.25 inches, by spaced turning bars which are controlled by web guides. The spaced and folded nonwoven webs are then fed into the extrusion laminating station and laminated by extrusion of a polyethylene film of 0.914 grams/cm$^3$. This polyethylene film of approximately 0.8 mils is extruded through a conventional extrusion die, at a melt temperature between 400°–600° F., into the nip rollers which press on the webs and polyethylene film with approximately 30–60 psi of pressure to achieve the desired bond strength of between 10 grams/inch to several hundred grams/inch of peel strength.

The laminate then enters a slitting station where slitting knives are located between the folded nonwoven webs to slit the polyethylene film. Accordingly, the 3.5 inch folded nonwoven webs are all laminated to polyethylene film of 3.75" wide. The 3.5 inch wide folded nonwoven web is laminated with polyethylene film with a 0.125 inch wide loose flap of polyethylene film on each side of the nonwoven which is not laminated to nonwoven.

The strip laminated, folded nonwoven is then unfolded and wound onto a roll for storage or later use.

EXAMPLE 11

The non-woven is slit and folded as in Example 10. However, the spacing between each folded web is adjusted to approximately 2 inches wide. The knives are located between adjacent folded nonwoven webs to slit the polymer into 11 inch widths. The result is a nonwoven web of 14 inch width is covered with a 5.5 inch wide polymeric film where 3.5 inches width of this film is laminated to the 3.5 wide folded nonwoven at the center of the web. The additional polyethylene film of 1" on opposite sides of the laminated nonwoven, which is not laminated to the nonwoven web, may be used to construct barrier cuffs to provide a self-contained pocket to confine body waste.

EXAMPLE 13

A carded polypropylene nonwoven fibrous web of 20 grams/yd$^2$ is loaded into the unwind position. A roll of polypylene film is loaded into a second unwind position. The polymer is unrolled and fed through a slitting station to form a multiple adjacent strips of polypropylene approximately 7 inches wide. The strips of polypropylen are then separated, by approximately 7 inches, by spaced turning bars which are controlled by web guides. The wide nonwoven web is then fed to the laminating station and laminated by patterned pressure rollers to the spaced strips of polypylene film at a pressure to achieve the desired bond strength anywhere between 10 grams/inch to several hundred grams/inch of peel strength.

The laminate then enters a slitting station where slitting knives are located between the strips of polyethylene film to slit the nonwoven material. The result is 14 inch wide nonwoven webs laminated to polyethylene film of 7 inches wide located at the center of the nonwoven strip.

EXAMPLE 14

A carded polypropylene nonwoven fibrous web of 20 grams/yd$^2$ is loaded into the unwind position. The wide web of this nonwoven roll is then fed through the slitting station to form multiple adjacent webs approximately 11 inches wide. Each 14 inch wide web is then folded approximately 2 inches from the free edges of slit nonwoven toward the center of the nonwoven. The folded nonwoven webs are steered to the desired spacing to each other, i.e., 7 inches wide, by spaced turning bars which are controlled by web guides. The spaced and folded nonwoven webs are then fed to an extrusion laminating station and laminated by extrusion of a polyethylene film of 0.914 grams/cm$^3$. This polyethylene film having a thickness of approximately 0.8 mils is extruded through a conventional extrusion die, at a melt temperature between 400°–600° F., into the nip rollers which press on the webs and polyethylene film with approximately 30–60 psi of pressure to achieve the desired bond strength of between 10 grams/inch to several hundred grams/inch of peel strength.

The laminate then enters a slitting station where slitting knives are located between the folded nonwoven webs to slit the polyethylene film. Accordingly, the 7 inch folded nonwoven webs are all laminated to polyethylene film of 14 inches wide. The 7 inch nonwoven web is laminated with polyethylene film with a 3.5 inch wide loose flap of polyethylene film on each side of the nonwoven which is not laminated to nonwoven. The strip laminated, folded nonwoven is wound directly onto a roll for storage or later use. The product of example 6 may be used as a polymer back-sheet of a diaper with the folded portion of the nonwoven forming a 2 inch standing leg cuff.

In Examples 1–15, the polyethylene film may be replaced by a microporous formable film composed of 30% to 40% polyethylene, 10%–15% of poly(ethylene-vinylacetate) copolymer, 40%–55% of stearic acid treated calcium carbonate and 5%–10% of glycerol monostearate. This nonwoven web with a center portion of the nonwoven laminated to the above microporous formable film can be interdigitately stretched on its CD and/or MD directions in the center portion of laminated area to form a microporous laminate in the center portion of this nonwoven web. The product accordingly is a fluid barrier in the center portion but is breathable to air, moisture, and moisture vapor due to its high degree of microporosity. The method of stretching is detailed in U.S. Pat. Nos. 5,296,184; 5,215,254,111 and 5,202,173 herein incorporated by reference in their entirety.

In a preferred form, the laminated sheet employs a thermoplastic film having a gauge or a thickness between about 0.25 and 10 mils and, depending upon use, the film thickness will vary and, most preferably, in disposable applications is on the order of about 0.25 to 2 mils in thickness. The nonwoven fibrous webs of the laminated sheet normally have a weight of about 10 grams per square yard to 60 grams per square yard preferably about 20 to about 40 grams per square yard, As indicated above, the composite or laminate may be used in many different applications such as baby diapers, baby training pants, catamenial pads, garments, and the like.

The present invention allows a continuous in-line process for introducing the web material to the laminator, for embossing and laminating strips or zones of polymer to non-woven in-line with high efficiency. For simplicity, extrusion laminating and dynamic mechanical bonding are shown in the figures and fully described in the specification, however, there are other possible laminating steps including adhesive laminating, spray laminating, gravure laminating, slot die laminating, ultrasonic laminating or thermal bond laminating.

As shown in FIG. 1, two rolls of nonwoven fibrous sheets 2, 3 of 5–70 grams per square yard may be loaded into the two position unwind station 1. The sheet 4 is unwound and fed into the apparatus. The end of a first roll 2 may be spliced to the beginning of the second roll 3 by a zero speed thermal splicer 5. Alternatively, the splice may be a zero speed tape splice or a flying tape splice. The sheet 4 engages a festoon 6 if a zero speed splice is desired. The sheet 4 is then slit by slitter 8 into narrow webs 9. The narrow webs 9 are adjacent after slitting. The narrow webs 9 are subsequently spaced apart by turning apparatus and web guides which are sequentially spaced down the longitudinal axes of the incoming narrow webs 9. By controlling the separation of the web slitters, it is possible to obtain laminates having different web widths, different final laminant widths, and unequal polymer overhang from each side of the narrow web.

Figure 3:
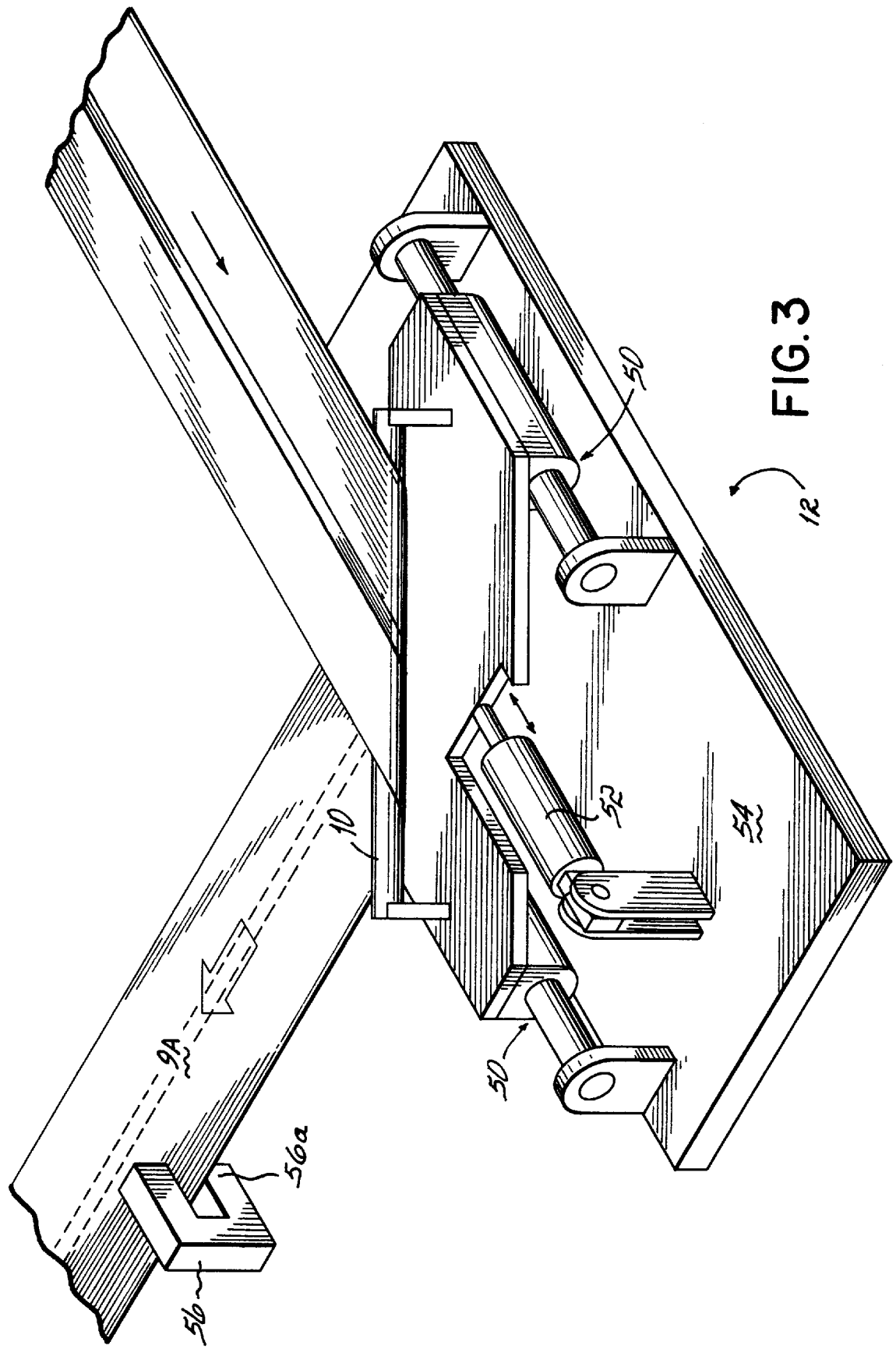
FIG. 3 is a schematic perspective view showing the combination turning bar and guiding mechanism.

The turning apparatus is preferably a series of turning bars 12 which lie in the plane of the incoming narrow webs 9. The webs are guided to the embossing and laminating station 15 by way of web guides 12. The web guides 12, shown in detail in FIG. 3, include an edge sensor 56 which optically senses the lateral deviation of the narrow web 9. The turning bar 10 is fixed to a mounting plate 54 by linear bearings 50. The edge sensor 56 is linked to actuator 52. Based upon a signal emitted from edge sensor 56, the actuator 52 moves the turning bar laterally on the linear bearings to compensate for any deviation of the narrow web 9. Embossing and laminating station 15 includes rollers 14, 16, an extruder 20 and a die 18 for extruding a sheet of polymer film 19 onto the narrow webs 9. The polymer film 19 and the narrow webs 9 are jointed at the nip of rollers 14 and 16. The polymer layer 19 is extruded from the die 18 at a temperature of about 500 to 625°. The extruded polymer film 19 is on the order of about 0.25 to 8 mils in thickness and is laminated at temperatures on the order of about 500 to 625°. The compressive force at the nip is controlled such that the webs are bonded to the polymer film. Pressures on the order of about 40 to 200 pli (pounds per linear inch) are sufficient to achieve satisfactory bond for fibrous webs of about 5–70 grams per square yard. The resulting laminate 21 of polymer film 19 and nonwoven webs 9 is then tensioned between spaced rollers 22 and 24 so that the laminate may be slit by blades 26 to form individual laminate webs 28.

The laminate webs 28 include a single web of nonwoven, woven or polymer material with a polymer layer adhered to one side of the web and overhanging the edges of the web. The overhanging edges may then be folded back to produce a laminated layer the width of the nonwoven web 9 with a polymer film 19 adhered to one side. The narrow laminated webs 28 may then be wound on a winder 30 for storage or future use.

Figure 2:
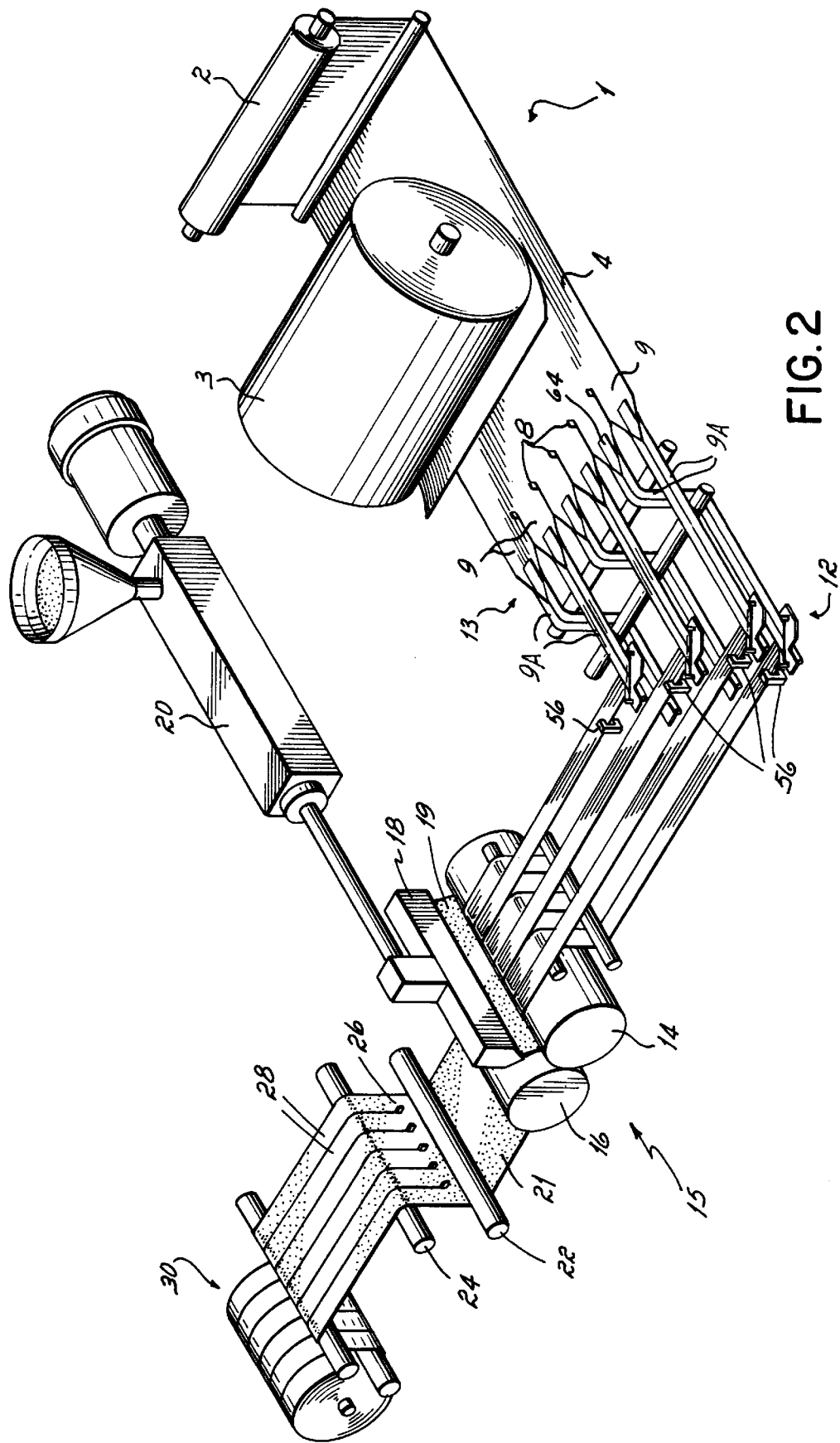
FIG. 2A is a diagrammatic perspective view of an in-line apparatus for slitting, folding, turning and spacing a non-woven web with subsequent extrusion laminating.
FIG. 2B is a diagrammatic perspective view of a double folding apparatus of the present invention.
Figure 2A:
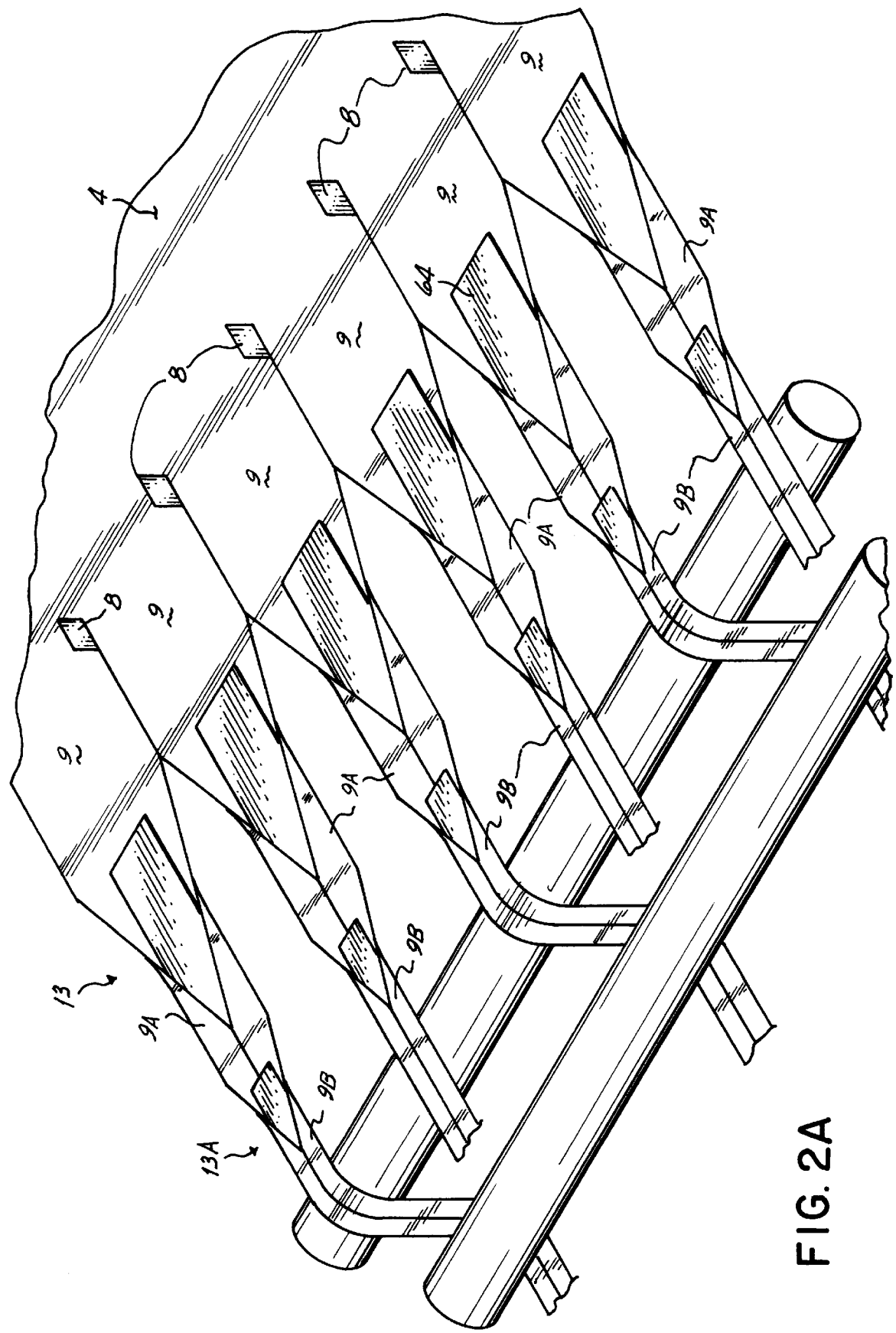

As shown in FIG. 2A, two rolls of nonwoven fibrous sheets 2, 3 of 5–70 grams per square yard may be loaded into the two position unwind station 1. The sheet 4 is unwound and fed into the apparatus. The end of a first roll 2 may be spliced to the beginning of the second roll 3 by a zero speed thermal splicer (as shown in FIG. 1). Alternatively, the splice may be a zero speed tape splice or a flying tape splice. The sheet 4 will engage a festoon if a zero speed splice is desired. The sheet 4 is then slit by slitter 8 into narrow webs 9. The narrow webs are adjacent after slitting. The narrow webs 9 are subsequently folded by folding apparatus 13 to form folded webs 9A and separated by a predetermined distance by turning apparatus 12 and web guides 56 which are sequentially spaced down the longitudinal axes of the incoming folded webs 9A. By controlling the separation of the web slitters, it is possible to obtain laminates having different web widths, different final laminant widths, and unequal polymer overhang from each side of the folded webs 9A.

The turning apparatus is preferably a series of turning bars 10 which lie in the planes of the incoming folded webs 9A. As discussed above with reference to FIG. 3, the webs are guided to the embossing and laminating station 15 by way of web guides 56. The web guides 56, shown in detail in FIG. 2, include an edge sensor 56a which optically senses the lateral deviation of the folded web 9. The turning bar 10 is fixed to a mounting plate 54 by linear bearings 50. The edge sensor 56a is linked to actuator 52. Based upon a signal emitted from edge sensor 56a, the actuator 52 moves the turning bar 10 laterally on the linear bearings to compensate for any deviation of the folded web 9. Embossing and laminating station 15 includes rollers 14, 16 an extruder 20 and a die 18 for extruding a sheet of polymer film 19 onto the folded web 9A. The polymer film 19 and the folded webs 9A are jointed at the nip of rollers 14 and 16. The polymer layer 19 is extruded from the die 18 at a temperature of about 350° to 625°. The extruded polymer film 19 is on the order of about 0.25 to 8 mils in thickness and is laminated at temperatures on the order of about 350° to 625°. The compressive force at the nip is controlled such that the webs are bonded to the polymer film. Pressures on the order of about 40 to 200 pli (pounds per linear inch) are sufficient to achieve satisfactory bond for fibrous webs of about 5–70 grams per square yard. The resulting laminate 21 of polymer film 19 and folded nonwoven webs 9A is then tensioned between spaced rollers 22 and 24 so that the laminate may be slit by blades 26 to form individual laminate webs 28 which are wound on winder 30.

Figure 6:
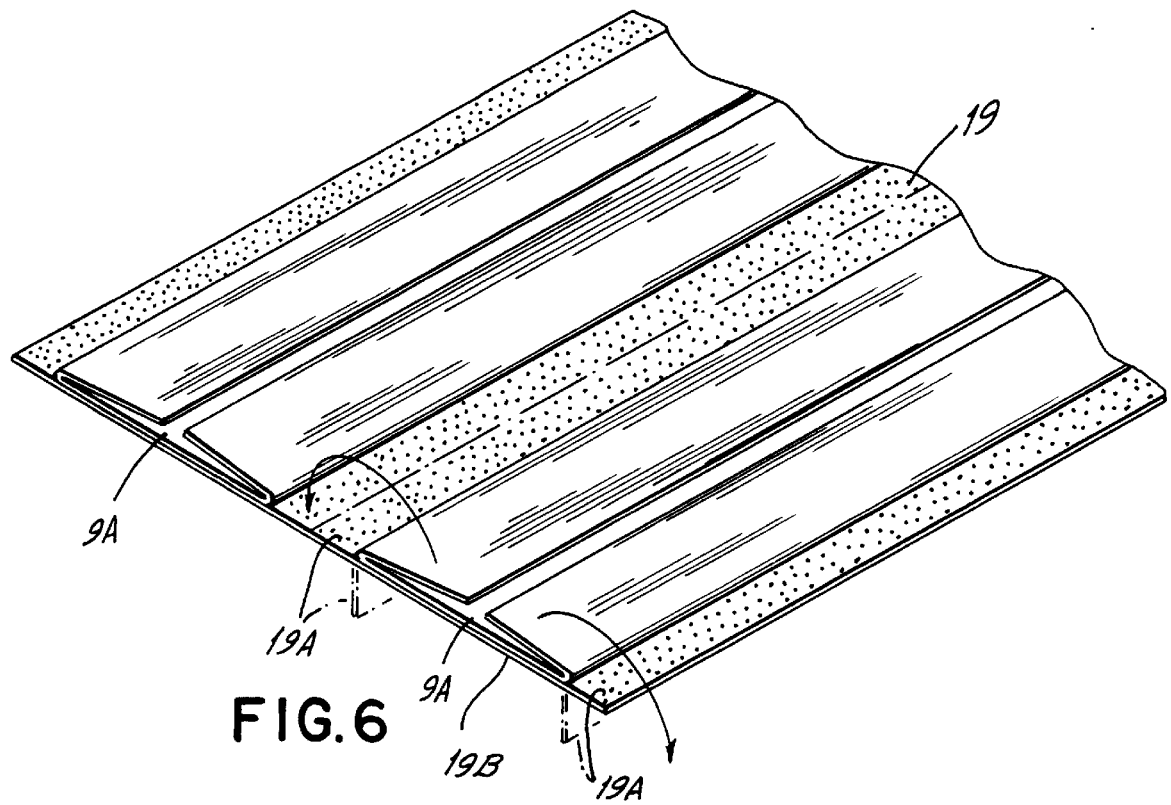
FIG. 6 is a schematic perspective view of folded nonwoven webs after lamination to polymeric film.
Figure 7:
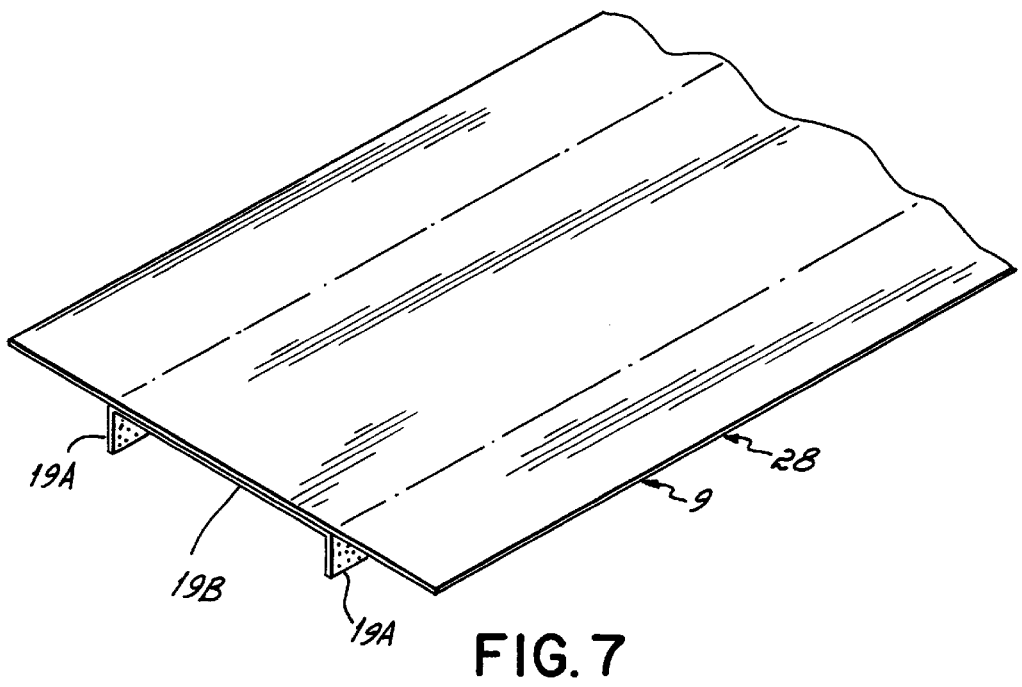
FIG. 7 is a schematic perspective view of a single nonwoven strip after slitting of the polymeric film and after unfolding.

The laminated webs 28 of polymer and nonwoven are shown in FIG. 6 prior to slitting and a single web, after slitting is shown in FIG. 7.

Figure 8:
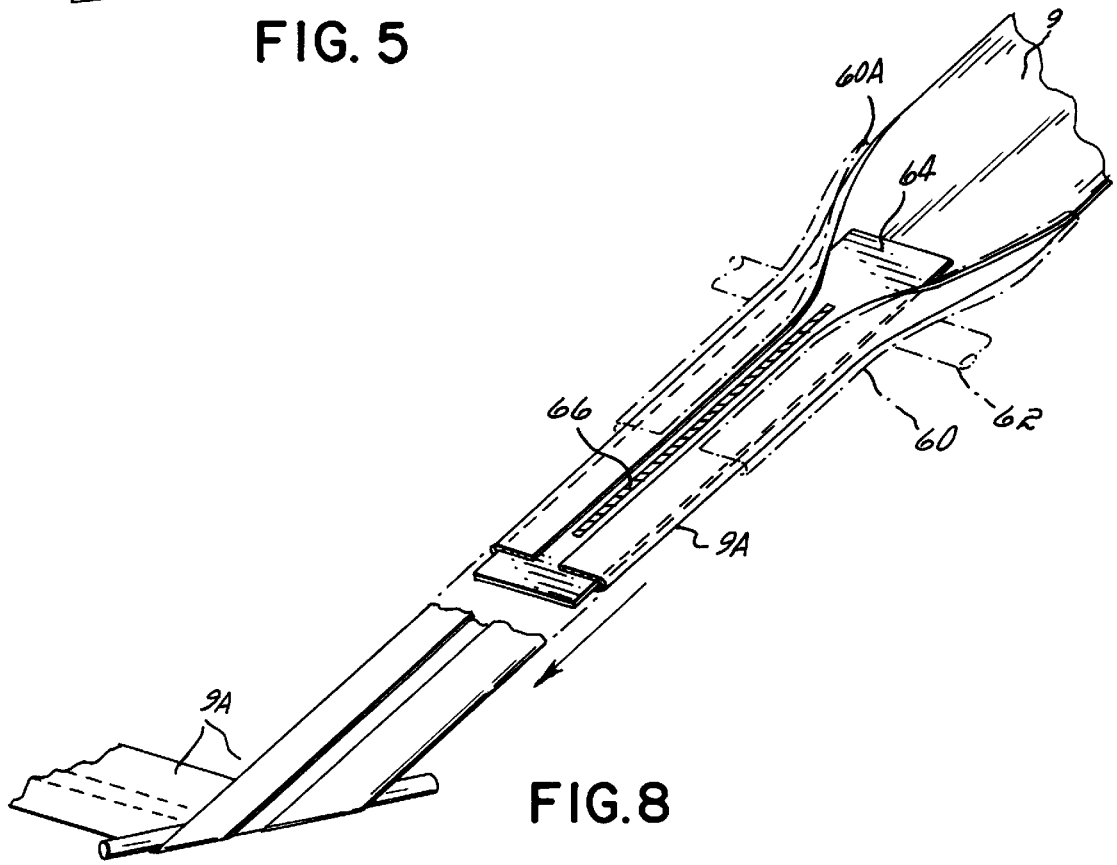
FIG. 8 is a diagrammatic perspective view of a folding apparatus of the present invention

A second embodiment of the present invention is shown in FIG. 2B. The incoming narrow web 9 is folded by a first folding apparatus 13 to form folded web 9A, which may approach approximately one half of the width of narrow web 9. The folded webs 9A are then folded by second folding apparatus 13A to form double folded web 9B, which may approach approximately one quarter the width of narrow web 9. The folding and unfolding apparatus 13 are shown in detail in FIGS. 4, 5, and 8. After leaving the slitter 8 narrow webs 9 contact a folding guide 60 and folding bar 64. Folding guide 60 is supported on support bar 62. Folding plate 64 is supported by folding plate support 66, shown cutaway for clarity. Folding plate support 66 extends along the longitudinal direction of the folding plate 64 and may serve as a guide to prevent overlapping of the free edges of the narrow web.

Figure 4:
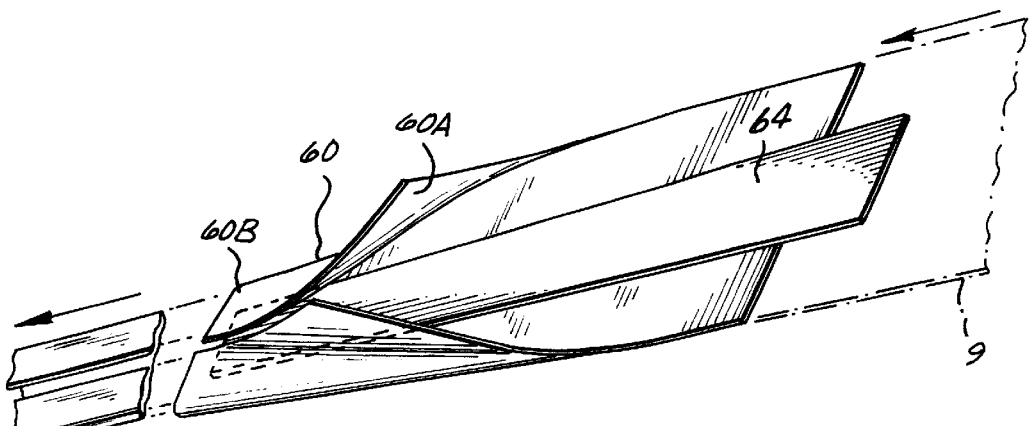
FIG. 4 is a schematic perspective view of a folding bar used in the present invention.

In FIG. 4 the incoming narrow web 9, shown in phantom, contacts the inner portion 60A of the folding guide 60. The lateral edges of the narrow web follow the contour of guide 60 and move up and over folding bar 64. The trailing portion 60B of folding guide 60 forces the free edges of narrow web 9 against folding bar 64.

Figure 5:
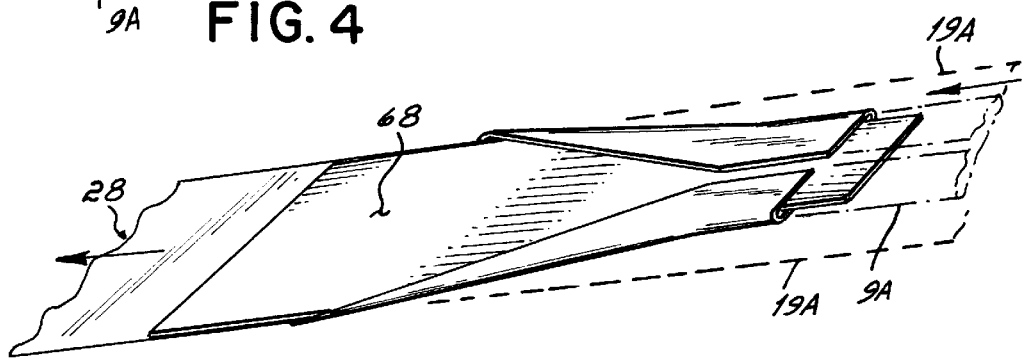
FIG. 5 is a schematic perspective view of an unfolding bar used in the present invention.

Prior to rolling the laminate 28 on winder 30 the folded nonwoven may be unfolded by unfolding bar 68, as shown in FIG. 5. During unfolding, folded web 9A of the incoming laminate 28 contacts unfolding bar. As the opposing flaps of the folded nonwoven 9A run along the increasing width of the unfolding bar the nonwoven material is unfolded. FIG. 5 also shows the loose polymer overhang 19A, both shown in phantom for clarity, of the extruded polymer 19.

The material produced by the present invention includes a wide section of nonwoven 9 which is extrusion laminated to a polymer film. FIG. 6 shows two strips of folded nonwoven material 9A laminated to polymer film 19. The final product 28, after slitting and unfolding, is shown in FIG. 7. The final product includes a strip of nonwoven 9 laminated to a portion of the polymer film 19B with loose polymer flaps 19A on either side of the laminated portion 19B.

Figure 9:
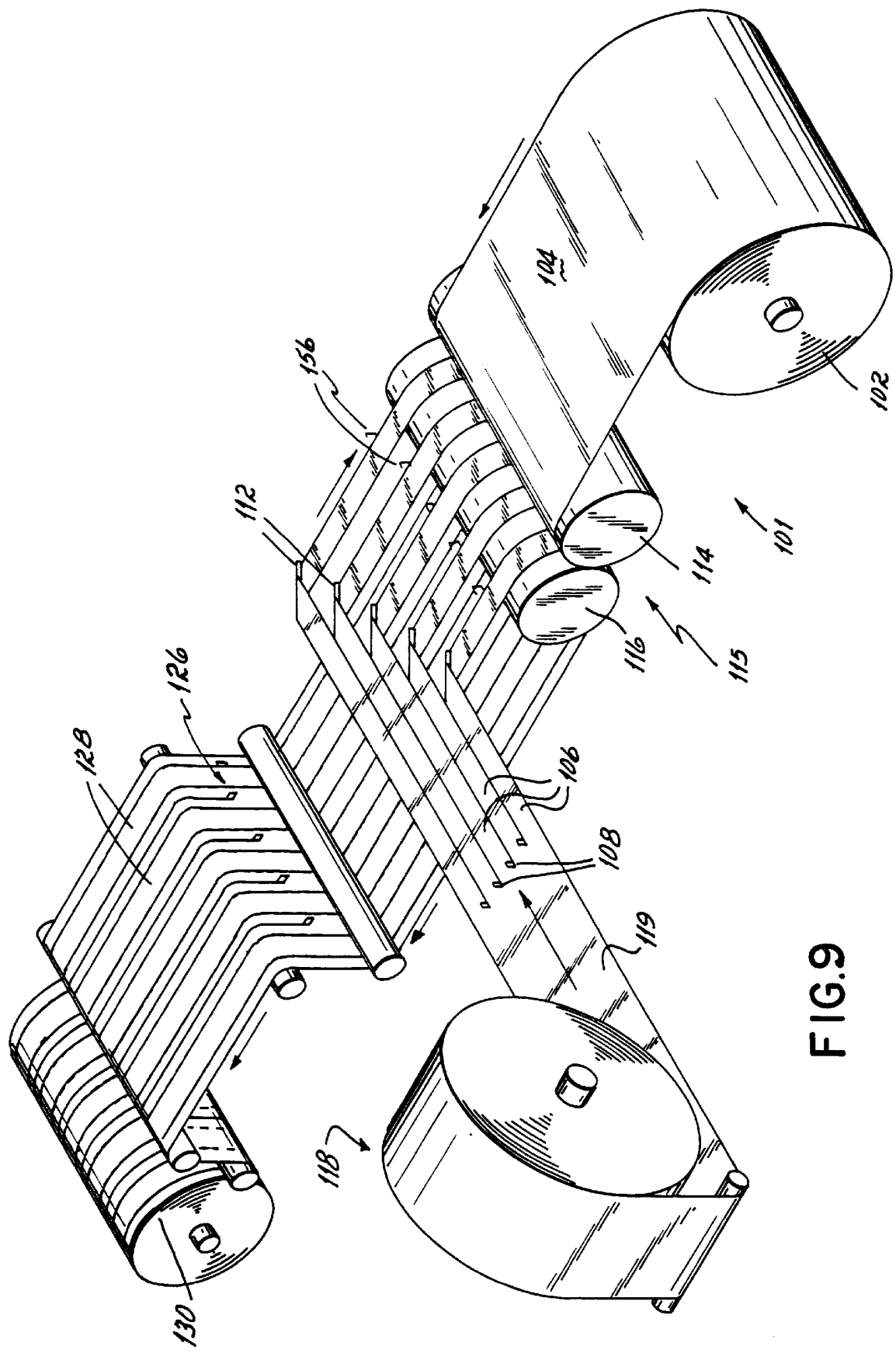
FIG. 9 is a diagrammatic perspective view of an in-line apparatus for slitting a polymer sheet, turning and spacing the polymer strips for lamination with a wide web of nonwoven.

Another embodiment of the present invention is shown in FIG. 9. A roll 102 of nonwoven fibrous sheet 104 is loaded into the unwind position 101. The end of roll 102 may be spliced to the beginning of a second roll (not shown) by a zero speed splice or a flying splice. If a zero speed splice is to be used, the web 104 should engage a festoon 6 (as shown in FIG. 1). A roll of a sheet of polymer film 119 is loaded into a second unwind position 118. The end of the sheet of polymer film 119 may be spliced to another roll by a zero speed or flying splice, as discussed above. As an alternative the sheet of polymer film 119 may be extruded through an extruder 20 (as shown in FIG. 1). The edges of the extruded film would be trimmed to proper size prior to or at slitting station 108. The polymer is unrolled and fed through a slitting station 108 to form multiple adjacent strips of polymer 106. The strips of polymer 106 are then separated by a predetermined distance by spaced turning bars 112 which are controlled by web guides 156. The turning bars 112 are similar to those shown in FIG. 3. The wide nonwoven web 104 is then fed to the laminating station 115 and laminated by heated pressure rollers 114 and 116 to the spaced strips of polymer film 106 at a pressure to achieve the desired bond strength.

The laminate then enters a slitting station 126 where slitting knives are located between the strips of polymer film to slit the nonwoven material. The resultant nonwoven webs are laminated to polymer film at the center of the nonwoven strip. The final product 128 is wound on take-up reel at winder station 130. This product is similar to that shown in FIG. 6, however there are no loose polymer flaps 19A at the outer edges of the laminated portion 19B.

While the invention has been described with reference to specific embodiments and examples herein, it is not intended that the invention be limited to such specifics. Various exchanges and modifications may occur to persons skilled in the art which are within the scope of the invention as defined in the appended claims.

What is claimed is:

1. An apparatus for in-line lamination of a non-woven fibrous sheet and an extruded polymer sheet to form a laminate, comprising:

a web slitter for dividing said non-woven fibrous sheet into a plurality of narrow non-woven fibrous webs;

a first plurality of folding means, each of the first folding means adapted to fold one of the plurality of narrow non-woven fibrous webs;

a plurality of spaced turning bars positioned at an oblique angle to the incoming folded narrow webs for turning each of said narrow webs such that the plurality of webs are separated by a predetermined distance; and an extrusion laminator for laminating an extruded polymer sheet on a surface of the separated non-woven fibrous webs to provide a laminate of said extruded polymer sheet and the separated webs and having a portion of the extruded polymer sheet between the non-woven fibrous webs.

2. The apparatus of claim 1 further comprising:

a second plurality of folding means, each of the second folding means adapted to fold one of the folded webs output from the first plurality of folding means.

3. The apparatus of claim 1 further comprising:

a plurality of unfolders, located downstream from said laminator, for unfolding the narrow webs.

4. The apparatus of claim 1 wherein said turning bars are equally spaced.

5. The apparatus of claim 1 wherein said turning bars are unequally spaced.

6. The apparatus of claim 1 further comprising:

a means for slitting the portion of the extruded polymer sheet between the separated webs.

7. The apparatus of claim 6 wherein said means for slitting is selected from the group consisting of a score slitter, shear slitter, razor slitter, water jet slitter and ultrasonic slitter.

8. The apparatus of claim 1 further comprising:

an unwind station for storing at least one roll of the non-woven fibrous sheet.

9. The apparatus of claim 8 wherein said unwind station is a two position unwind station.

10. The apparatus of claim 1 further comprising:

an automatic splicing means.

11. The apparatus of claim 10 wherein said automatic splicing means is selected from the group consisting a zero speed thermal splicer, zero speed tape splicer and flying tape splicer.

12. The apparatus of claim 1 wherein said turning bars include a means for guiding the plurality of webs from said turning bars to said laminator.

13. The apparatus of claim 1 further comprising:

a take-up reel for receiving the laminate.

14. The apparatus of claim 1 wherein said non-woven fibrous sheet is selected from the group consisting of polypropylene and copolymers thereof.

15. The apparatus of claim 1 wherein the non-woven fibrous sheet is carded.

16. The apparatus of claim 1 wherein said non-woven fibrous sheet has a weight from about 5 to 70 grams/yd$^2$.

17. An apparatus for in-line lamination of a non-woven fibrous sheet and an extruded polymer sheet to form a laminate, comprising:

a web slitter for dividing said non-woven fibrous sheet into a plurality of narrow non-woven fibrous webs;

a first plurality of folding means, each of the first folding means adapted to fold one of the plurality of narrow non-woven fibrous webs;

a plurality of spaced turning bars positioned at an oblique angle to the incoming folded narrow webs for turning each of said narrow webs such that the plurality of webs are separated by a predetermined distance; and an extrusion laminator for extruding a polymer sheet into a nip of opposed rollers to bond the extruded polymer sheet on a surface of the separated non-woven fibrous webs to provide a laminate of said extruded polymer sheet and the separated webs and having a portion of the extruded polymer sheet between the non-woven fibrous webs.

18. The apparatus of claim 17 wherein said turning bars are unequally spaced.

19. The apparatus of claim 17 wherein said non-woven fibrous sheet is selected from the group consisting of polypropylene and copolymers thereof.

20. The apparatus of claim 19 wherein the non-woven fibrous sheet is carded.

21. The apparatus of claim 17 wherein said non-woven fibrous sheet has a weight from about 5 to 70 grams/yd$^2$.

22. The apparatus of claim 12 further comprising:

a second plurality of folding means, each of the second folding means adapted to fold one of the folded webs output from the first plurality of folding means.

23. The apparatus of claim 17 further comprising:

a plurality of unfolders, located downstream from said laminator, for unfolding the narrow webs.

* * * * *

UNITED STATES PATENT AND TRADEMARK OFFICE
CERTIFICATE OF CORRECTION

PATENT NO. : 5,942,080
DATED : August 24, 1999
INVENTOR(S) : Robert M. Mortellite, Kevin W. Preston, Thomas G. Mushaben It is certified that error appears in the above-indentified patent and that said Letters Patent is hereby corrected as shown below:

Column 1, Line 8 "WEBB" should read --WEBS--.

Column 2, Line 35, "FIG. 2A" should read --FIG. 2--.

Column 2, Line 38, "FIG. 2B" should read --FIG. 2A--.

Column 7, Line 59, "5,215,254,111" should read --5,254,111--.

Column 11, Line 2, "consisting a zero" should read --consisting of a zero--.

Column 12, Line 39, "12" should read --17--.

Signed and Sealed this

Third Day of April, 2001

Attest:

NICHOLAS P. GODICI

*Attesting Officer*   *Acting Director of the United States Patent and Trademark Office*